United States Patent [19]

Arnold et al.

[11] Patent Number: 4,914,209

[45] Date of Patent: Apr. 3, 1990

[54] PYRAZOLOTRIAZOLES AND PROCESSES FOR THEIR FORMATION

[75] Inventors: Robert W. Arnold; Cataldo A. Maggiulli, both of Rochester, N.Y.

[73] Assignee: Eastman Kodak Company, Rochester, N.Y.

[21] Appl. No.: 313,561

[22] Filed: Feb. 22, 1989

[51] Int. Cl.$^4$ ............................................. C07D 249/00
[52] U.S. Cl. .................................. 548/262.4; 548/258
[58] Field of Search .................................. 548/258, 266

[56] References Cited

U.S. PATENT DOCUMENTS 3,725,067 4/1973 Bailey et al. .
4,621,046 11/1986 Sato ..................................... 548/266
4,710,453 12/1980 Hirabayashi ........................ 548/258

FOREIGN PATENT DOCUMENTS 2033177 2/1987 Japan .................................... 548/266
3150284 6/1988 Japan .................................... 548/266
1458528 12/1976 United Kingdom ................ 548/266

OTHER PUBLICATIONS

Research Disclosure No. 169, May 1978, entry 16940.
Goddard in Chem. Abstr., vol. 89, entry 112295(u), 1978.
Chem. Abstr., vol. 109, entries 180315q and 11955q (1988).

*Primary Examiner*—Donald G. Daus
*Attorney, Agent, or Firm*—Robert A. Linn

[57] ABSTRACT

A 1,7-diacetylpyrazolotriazole was prepared by acid catalyzed acetylation of 6-methyl-3-[3-(4-nitrophenyl)-propyl]-1H-pyrazolo[5,1-C]-1,2,4-triazole. Hydrolysis gave the 7-acetylpyrazolotriazole. Oxidation converted the 7-acetylpyrazolotriazole to a 7-acetoxypyrazolotriazole.

12 Claims, No Drawings

PYRAZOLOTRIAZOLES AND PROCESSES FOR THEIR FORMATION

FIELD OF THE INVENTION

This invention relates to certain pyrazolo-1,2,4-triazoles, to analogous (isomeric) pyrazolo-1,3,4-triazoles, and to process for their formation.

BACKGROUND OF THE INVENTION

It is known in the photographic arts that photographic elements can produce dye images through the selective formation of dyes. It is also known that the dyes can be formed by reacting (i.e. coupling) a color-developing agent such as a primary aromatic amine in its oxidized form, with a dye-forming coupler. It is also known that pyrazolotriazoles constitute one type of dye-forming coupler which can form subtractive primary (yellow, magenta, and cyan) image dyes.

Because of the utility of pyrazolotriazoles as dye couplers, new pyrazolotriazole starting materials, and new processes for preparing them are always of interest in the art.

In the course of work conducted in connection with the development of this invention, an attempt was made to synthesize 1-acetyl-[6-methyl-3-[3-(4-nitrophenyl) propyl]-1H-pyrazolo[5,1-C]-1,2,4-triazole, by acetylation of 6-methyl-3-[-(4-nitrophenyl) propyl]-1H-pyrazolo[5,1-C]-1,2,4-triazole in boiling acetic anhydride. Surprisingly, it was found that the pyrazolotriazole acetylated at the 7-carbon, as well as at the 1-nitrogen. An attempt was made to repeat this unexpected reaction using 6-methyl-3-[3-(4-nitrophenyl) propyl]-1H-pyrazolo-[5,1-C]-1,2,4-triazole prepared by another method. The results were different, i.e. the diacetylation was not repeated, only monoacetylation occurred. Further experimentation showed that the 1,7-diacetylation requires the presence of an acid catalyst.

Thus, it appears (a) that the 6-methyl-3-[3-(4-nitrophenyl) propyl]-1H-pyrazolo-[5,1-C]-1,2,4-triazole which gave the disacetylation contained a catalytic amount of an acid catalyst, (b) that this acid catalyst was introduced during preparation of the pyrazolotriazole, and (c) that it therefore yielded the 1,7-diacetyl product without the addition of more acid.

Subsequent work has also showed that the 1,7-diacetyl compound is a valuable intermediate for the preparation of other triazoles. Such use of the 1,7-diacetyl compound and related compounds is discussed and exemplified below, and constitutes part of this invention.

SUMMARY OF THE INVENTION

This invention relates to compounds which have the following basic structure:

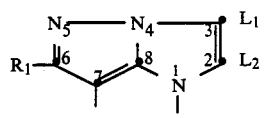

wherein
L₁ and L₂ are each a linking atom or group selected from N and C-R₂;
such that when L₂ is a nitrogen, L₁ is a ring carbon which is bonded to R₂, and the compound is a pyrazolo-1,2,4-triazole with substituents (R₁ and R₂) in the 3-position and the 6-position. When L₂ is C-R₂, L₁ is nitrogen, and the compound is a pyrazolo-1,3,4-triazole with substituents in the 2- and the 6-position.

In the compounds of this invention there are substituents bonded to the nitrogen and the carbon atoms in the 1-position and 7-position, respectively. With regard to the 7-position, the substituent is a hydrogen, hydroxy, acyl, acyloxy or sulfonyl radical. The substituent at the 1-position may be hydrogen, or an acyl, acyloxy or sulfonyl radical, such that only one of the substituents on the 1-position and 7-position is hydrogen.

Preferred compounds of this invention include compounds of the following types:

TYPE 1—Wherein the groups bonded to the 1-nitrogen and the 7-carbon through the unsatisfied valence lines in Formula I are selected from acyl and sulfonyl groups; i.e.

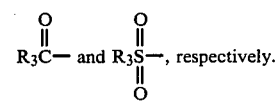

TYPE 2—Wherein a hydrogen is bonded to the 1-nitrogen, and the 7-carbon is bonded through the valence line in FIG. 1 to a group selected from acyl, sulfonyl, hydroxyl and acyloxy, i.e.

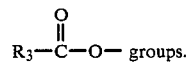

The radical R₃ within the formulas above, is defined in the discussion below.

Compounds of Type I, wherein the substituents attached to the 1-nitrogen and the 7-carbon are both acyl radicals, can be made by reacting (a) the starting compound of formula I (having hydrogen radicals attached at both the 1-position and the 7-position) with (b) an acylating agent, in the presence of (c), a catalytic quantity of a Bronsted or Lewis acid.

Compounds of Typ5 1 wherein the substituents at the 1-position and the 7-position are both sulfonyl groups R, can be made by reacting (a) the aforementioned starting material of Formula I, with (b) a sulfonylating agent, in the presence of (c) a base.

Compounds of Type 2 can be made by a sequence of reactions, of which the first is preparation of a compound of Type 1, followed by hydrolysis of an acyl or sulfonyl group to remove it from the 1-position, so that the 1-nitrogen becomes bonded to hydrogen. The substituent on the 7-carbon remains.

When the resultant compound has an acyl group at the 7-position, it can be reacted with a oxidant, such as a composition comprising a salt of peroxymonosulfuric acid, $H_2SO_5$, to form an acyloxy group at the 7-position. The acyloxy group can be subsequently hydrolyzed to replace it with a hydroxy radical.

Compounds of this invention can be further reacted to form pyrazolotriazoles which are useful as dye couplers in the photographic arts. Other compounds of this invention serve as chemical intermediates for preparing compounds useful as dyes, pharmaceuticals, agricultural chemicals, or fine chemicals which are useful as intermediates or have other utilities.

DESCRIPTION OF PREFERRED EMBODIMENTS

In one embodiment, this invention relates to Type I compounds, i.e. 1,2,4-triazoles and 1,3,4-triazoles having formula I above, wherein the 1-nitrogen and the 7-carbon are both substituted with a radical having the formula $R_3$-E, wherein E is selected from the class consisting of the carbonyl radical,

and the sulfonyl radical,

$R_1$, $R_2$ and $R_3$ are inert substituents. (See Formula I above for the location of the $R_1$- and $R_2$-substituents in the pyrazolotriazoles of this invention).

In preferred compounds of this embodiment, $R_1$ is a hydrocarbyl radical, i.e. a radical solely composed of carbon and hydrogen, and $R_2$ is an alkyl radical substituted with a nitrophenyl group, viz

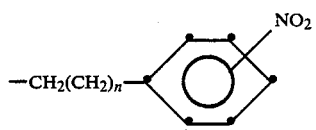

Although not bound by any theory, it is believed the diacyl and the disulfonyl compounds of Type I are formed by a monoacylation or monosulfonylation, followed by introduction of the second acyl or sulfonyl group. It is also believed that acylation first occurs at the 1-position, followed by acylation at the 7-position. In the case of sulfonylation, it is believed that substitution first occurs on the 7-carbon atom, followed by introduction of the second sulfonyl group at the 1-position. It is to be understood however, that this invention is not critically dependent on a sequential substitution, or on any particular order of substitution.

However, a skilled practitioner can take advantage of the sequential substitution and stop the process at the stage where only monoacylation or monosulfonylation occurs, thereby forming unsymmetrical compounds which can be further reacted by subsequent processes as illustrated below.

This invention extends to Type I compounds having Formula I above, wherein an acyl group is bonded at the 1-position or the 7-position, and a sulfonyl group is present on the position in which the acyl group does not appear. Thus for example, one may acylate both the 1-position and the 7-position, then hydrolyze the acyl group in the 1-position, and subsequently replace it with a sulfonyl group, thereby forming a compound of this invention having an acyl radical in the 7-position, and a sulfonyl group in the aforementioned 1-position.

In another embodiment, this invention comprises compounds of Type 2, i.e. compounds of Formula I wherein a hydrogen is bonded to the nitrogen in the 1-position, and the carbon in the 7-position is substituted with a group selected from the acyl, acyloxy, sulfonyl and hydroxy radicals (alkoxy, aryloxy, etc.).

As already clear from the above discussion, this invention comprises compounds having the following basic structures:

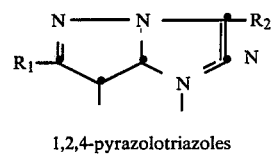

1,2,4-pyrazolotriazoles

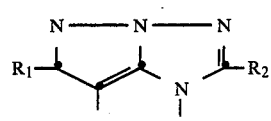

1,3,4-pyrazolotriazoles

In addition to the fused rings, these basic structures comprise inert substituents bonded to one or two carbon atoms and a nitrogen within the heterocyclic rings, as shown.

For the purpose of this invention, an "inert substituent" or "inert organic group" is defined by having the following characteristics:

(1). It is stable, or substantially stable, under the process conditions employed to prepare a compound of this invention: i.e. it does not decompose to an untoward extent during process(es) employed in this invention.

(2). It is non-reactive, or substantially non-reactive toward the other reagents employed to prepare a compound of this invention; i.e. it does not undergo an extraneous side reaction (to an unacceptable extent) with the other ingredient(s) used in the preparation of a compound of this invention.

(3). It does not prevent, by steric hindrance or other mechanism or effect, the formation of a compound of this invention.

Thus, a wide variety of substituents may appear as $R_1$ and/or $R_2$ in the above formula. In other words, this invention is not critically dependent on the type(s) of groups designated $R_1$ and $R_2$, so long as the groups meet criteria (1), (2) and (3). Typically, $R_1$ and $R_2$ are hydrogen or hydrocarbyl groups, i.e. groups which are solely composed of carbon and hydrogen. However, it is not necessary that $R_1$ and $R_2$ be solely composed of carbon and hydrogen; thus groups which comprise:

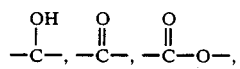

—$NH_2$, $NHR_1$, $NR_1R_1$, —$SO_2$—, —S—, —S—S—, and alkoxy, aryloxy, the like, can appear in compounds of this invention, so long as the substituents meet the three criteria enumerated above. Alkyl, cycloalkyl, alkenyl, cycloalkenyl, aryl, alkaryl and aryl groups which meet the critera can be present in the compounds of this invention. These may be hydrocarbyl, or substituted hydrocarbyl groups, as discussed above. For convenience, $R_1$ and $R_2$ are usually hydrogen or hydrocarbyl groups having up to about 20 carbon atoms; preferably they are hydrogen or alkyl or aryl groups of this type. Lower alkyl radicals (alkyl radicals with up to about 6 carbon atoms) and the phenyl radical are highly preferred.

When the radical $R_3$ appears in compounds of this invention, it has the same criteria, and may be selected from the same radicals, as $R_1$ and $R_2$ (see above). Preferably, $R_3$ is hydrogen, or an alkyl or aryl radical of up to about 20 carbon atoms. In compounds of this invention $R_1$, $R_2$ and $R_3$ may all be alike, or different. Likewise, any two may be alike.

The $R_1$, $R_2$ and $R_3$ radicals are generally selected according to the properties that they confer on the compounds, and/or the role that they play in the selected utility. For example, if the radical $R_3$ appears in a group which is to be subsequently removed by hydrolysis, then $R_3$ may be a methyl or ethyl group in order to lower process costs. If $R_1$ is present solely for blocking purposes in order to prevent attack at the 6-position during subsequent chemical processing, then $R_1$ may be selected from lower alkyl radicals, e.g. —$CH_3$, or other alkyl radical having up to about 6 carbon atoms.

On the other hand, the size or nature of the group may be selected because it is produced in a convenient reaction for preparing the pyrazolotriazole starting compound, or the group may be selected to confer some physical or chemical property, such as a desired degree of solubility, or a desired degree of compatibility with other ingredients in a mixture in which the product is used.

Moreover, one or more of the radicals $R_1$, $R_2$ or $R_3$ may be selected to contain a radical which contains a reactive site. For example, $R_2$ may be a group having the formula

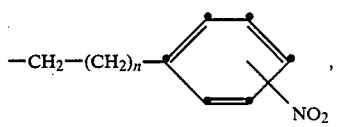

wherein
n is a whole number equal to 0 to about 6, and
the nitro group is ortho, meta or para to the alkyl side chain. For some uses, it is desirable to subsequently reduce the aryl nitro group to an amino group. Accordingly, it is to be understood that the term "inert" in the phrase "inert substituent " does not mean that the substituent is unreactable in processing conducted after the compound is made.

To illustrate the process of this invention for preparing a compound have two acyl groups, one bonded to the 1-nitrogen, and the other bonded to the 7-carbon, the following example is presented.

EXAMPLE 1

Preparation of
1,7-Diacetyl-6-methyl-3-[3-(4-nitrophenyl)propyl]-1H-pyrazolo[5,1-C]-1,2,4-triazole A solution of 150 g (0.526 mole) 6-methyl-3-6-methyl-3-[3-(4-nitrophenyl) propyl]-1H-pyrazolo-[5,1-C]-1,2,4-triazole dissolved in 500 mL of acetic anhydride with 5 mL methanesulfonic acid, was boiled under reflux for 2 hours in a 1 L round bottom flask equipped with a thermometer, sweep stirrer, and a coil condenser. The flask was set in a heating mantle. After reaction, the solution was cooled to 30° C. and poured into 2500 mL of ice water in a 4 L beaker, with vigorous stirring. The mixture was stirred for ½ hour. The solid precipitate was collected on a Buchner funnel, washed with water, and then heptane. After drying in a hot air oven, the yield of the above named product was 177 g (91.1.%).

| Analysis | |
|---|---|
| Appearance: | tan powder. |
| m.p.: | 128°–133° C. |
| IR, NMR: | consistent with proposed structure. |
| MS: | consistent with proposed structure. |
| TLC: | eluted on silica gel with 45 toluene:30 dioxane: 1 methanol. |

Starting Material, $R_f$ 0.60, none detected.
Product, $R_f$ 0.65, exclusive component.

The product formed a magenta dye with an oxidized developer, while the starting material did not form a dye with that oxidized developer. This comparison in chemical properties confirms that the process of the example produced a product different from the starting material, and also illustrates a utility of a compound of this invention.

The above process may be conducted on other pyrazolo-1,2,4-triazoles and the isomeric pyrazolo-1,3,4-triazoles as discussed above; e.g. such compounds wherein $R_1$ is an alkyl or aryl group of 1 to 20 carbons, $R_2$ is

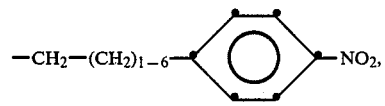

and $R_3$ is an alkyl or aryl group of 1 to 20 carbon atoms.

The acylating agent selected need not be an anhydride; it may be an acid or an acyl halide. Thus the acylating agent may have the formula:

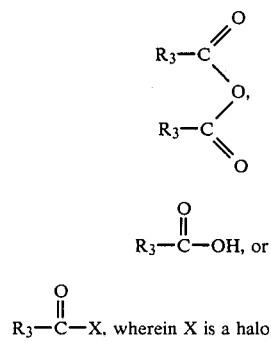

$R_3$—C—X, wherein X is a halogen, preferably chlorine or bromine.

The acylation may be conducted in the presence of a solvent or inert liquid reaction medium such as toluene, benzene, methylene chloride, and the like. The acylating agent may be used in solvent quantities, or stoichiometric or substantially stoichiometric quantities. Generally speaking, when an acid or anhydride is used, an excess of the acylating agent is employed in order to assist the reaction. There is no real upper limit on the amount of acylating agent; this being defined by such secondary characteristics as economics, size of the reaction vessel, ease of separation of product from the reaction mixture, ease of recovery of the unreacted acylating agent, etc.

The process may be conducted in the presence of a catalytic quantity of a Bronsted or Lewis acid. For the purpose of this invention, a Bronsted acid is any proton donor which donates a proton and does not hinder the process. Such materials are generally selected from alkyl sulfonic acids, hydrogen halides, sulfuric acid, and carboxylic acids such as those acids mentioned above for use as acylating agents. Lewis Acids, such as those employed for Friedel-Crafts acylations, e. c. $AlCl_3$, $FeCl_3$ $BF_3$, HF, $H_3PO_4$ and the like, can also be used as catalysts.

Generally speaking, a catalytic amount of such catalyst, e.g. from about 0.05 to about 0.25 moles per mole of starting triazole is used. Greater or lesser amounts can be employed if they afford the desired result. [By omitting the catalyst, a monoacylated product can be prepared].

The acylation may be conducted at any convenient temperature which gives a reasonable rate of reaction, and which does not cause an undue amount of decomposition of one or more of the ingredients employed. Generally speaking, a temperature within the range of from about 20° C. to about 200° C. is employed; more preferably the temperature is from about 100° C. to about 150° C.

Ambient pressure is generally satisfactory. Higher pressures, up to 100 atmospheres or more can be used if one of the reagents is a gas or vapor at the reaction temperature.

The process is generally conducted in the substantial absence of water to prevent unwanted hydrolysis. If hydrolysis is desired, the reaction can be conducted in the presence of a suitable amount of water. Preferably the hydrolysis is conducted subsequent to acylation, as demonstrated in Example 3. Subsequent hydrolysis is particularly efficacious when an acid anhydride or acyl halide is used as the acylating agent.

The reaction time is not a completely independent variable, but is dependent at least to some extent on the other reaction conditions employed, and the inherent reactivity of the reactants. In general, higher reaction temperatures require shorter reaction times. The process is usually complete in from about 0.5 to about 24 hours.

EXAMPLE 2

Preparation of
1,7-dimethylsulfonyl-6-methyl-3-[3-(4-nitro-phenyl)-propyl]-1H-pyrazolo[5,1-C]-1,2,4-triazole To a slurry of 2.85 grams (10 millimoles) of 1,7-dimethylsulfonyl-6-methyl-3-[3-(4-nitro-phenyl)propyl]-1H-pyrazolo[5,1-C]-1,2,4-triazole in 40 ml of methylene chloride stirred at 0° C., was added 1.51 grams (15 millimoles) of triethylamine, followed by 1.26 grams (11 millimoles) of methanesulfonyl chloride. The sulfonyl chloride was added dropwise over a two minute period. The resultant mixture was stirred for an additional 18 hours. Thin layer chromatography (TLC) indicated that some starting material still remained in the reaction mixture.

Accordingly, more triethylamine (1.51 grams, 15 millimoles) and methanesulfonyl chloride (1.26 grams, 11 millimoles) was added. The mixture was stirred an additional ½ hour; TLC indicated that no starting material was then present. The resultant mixture was filtered. The solid was washed with methylene chloride, isopropanol, H₂O, and isopropanol, and then dried in vacuo for 20 hours. This yielded 1.19 grams of the above-mentioned di(methanesulfonyl) product; m.p. 195°–197° C.

The filtrate, after washing with $H_2O$ and dilute Hcl, was dried over $MgSO_4$, treated with carbon, and evaporated. The residual solid was slurried in 35 ml of isopropanol for 20 hours, collected, and then washed with isopropanol and dried. An additional 2.38 grams of the above-named di(methanesulfonyl) product was obtained.

The product was also obtained by the same reaction conducted in tetrahydrofuran at room temperature for 3 hours. The product was isolated by pouring into water.

The above illustrates the disulfonylation process of this invention. Generally speaking, it can be conducted using as a starting material, any of the triazoles which are useful in the diacylation discussed above.

Generally, for sulfonylation one uses enough base to react with the hydrogen removed, i.e. at least about 1 or 2 moles of base per mole of starting triazole depending on the degree of sulfonation desired. The base can be used in excess of this amount; so can the sulfonylating agent. The amount of sulfonylating agent and base have no real upper limit, and the secondary considerations mentioned above (when discussing the amount of acylating agent) are applicable.

The reaction temperature, pressure, and time and other reaction parameters are similar to those discussed above for acylation.

The diacyl and disulfonyl products of this invention can be subjected to hydrolysis to remove an acyl or sulfonyl group substituted on the 1-nitrogen. To illustrate such a hydrolysis, the following example is presented.

EXAMPLE 3

Preparation of
7-acetyl-6-methyl-3-[3-(4-nitrophenyl)-propyl]-1H-pyrazolo[5,1-C]-1,2,4-triazole A slurry of 100 g (0.27 mole) of the product of Example 1, 500 mL methanol, and 25 mL of concentrated hydrochloric acid was boiled under reflux for 15 minutes in a 1 L round bottom flask equipped with a thermometer, sweep stirrer, and a coil condenser. The slurry never became a complete solution. The slurry was cooled to 5° C. in an ice bath. The solid was collected on a Buchner funnel and washed with cold methanol. After drying in a hot air oven, the yield of the above mentioned 7-acetyl product was 73.0 g (82.4%).

| Analysis | |
|---|---|
| Appearance: | white powder. |
| m.p.: | 191°–193° C. |
| IR, NMR: | consistent with proposed structure. |
| TLC: | eluted on silica gel with the system (45 toluene:30 dioxane:1 methanol). |
| 1-acetyl-[6-methyl-3-[3-(4-nitro-phenyl) propyl]-1H-pyrazolo[5,1-C]-1,2,4-triazole | R$_f$0.60 none detected. |
| Product of Example 1 | R$_f$0.65, none detected. |
| Product of this Example | R$_f$0.57, exclusive component. |

The 7-acetyl product did not form a magenta dye with oxidized developer, thereby confirming that the product of this invention differs from the 1,7-diacetyl starting material.

In general, the reaction conditions for the hydrolysis are not critical, and a practitioner can devise a similar, suitable procedure using the teachings of the above examples and the ordinary skill of the art.

Such hydrolysis reactions can be conducted using many of the 1-7 diacyl, and 1,7-disulfonyl compounds prepared by the diacylation and disulfonylation processes of this invention which are illustrated above.

EXAMPLE 4

Preparation of 7-Acetoxy-6-methyl-3-[3-(4-nitrophenyl)-propyl]-1H-pyrazolo[5,1-C]-1,2,4-triazole A paste of 162.5 g (1.25 equiv.) of a commercially available oxidant mixture having a composition substantially conforming to $2KHSO_5 \cdot KHSO_4 \cdot K_2SO_4$, and 162.5 mL sulfuric acid was prepared by hand-mixing with a stainless steel spatula in a 500 mL beaker. The paste was added in small portion to a slurry of 62.8 g (0.192 mole) of the product of Example 3 and 350 mL acetic acid in a 1 L Erlenmeyer flask set on a magnetic stirrer. The reaction was immersed in an ice bath to maintain a reaction temperature below 35° C. The addition was complete after 45 minutes. The slurry was stirred an additional 30 minutes at 25° C.

The slurry was poured into two liters of ice water in a 4 L beaker, while using vigorous stirring. The organics were extracted with three 300 mL portions of ethyl acetate. The combined extracts were dried over magnesium sulfate, and filtered through a silica gel pad on a Buchner funnel. The filtrate was concentrated to an oil and crystallized from 100 mL ethanol. After drying in a hot air oven, the yield of the 7-acetoxy product was 21 g (32%).

| Analysis | |
|---|---|
| Appearance: | tan powder |
| mp: | 128°-133° C. |
| IR, NMR: | consistent with proposed structure. |
| MS: | consistent with proposed structure. |
| TLC: | eluted on silica gel with system (45 toluene:30 dioxane:1 methanol). |
| Product of Example 3, | $R_f$ 0.57 none detected. |
| Product of Example 4, | $R_f$ 0.62 major component; several low $R_f$ impurities were detected in trace amounts. |

The product of this Example formed a magenta dye with oxidized developer demonstrating the utility of the compound.

This example demonstrates that products of this invention having an acyl group in the 7-position, can be oxidized to the corresponding 7-acyloxy compound reaction with by peroxymonosulfuric acid, or a salt thereof, e.g. an alkali metal salt such as the sodium or potassium salt, or an oxidant mixture such as $K_2S_2O_8$, $H_2SO_4$ and $K_2SO_4$, or a mixture such as $2KHSO_5 \cdot KHSO_4 \cdot K_2SO_4$, or a mixture similar to the material disclosed in U.S. No. 2,802,722.

When conducting the oxidation one uses at least about 1 mole of oxidant (e.g. persulfuric acid or Caro's acid, or salt thereof) per each one mole portion of pyrazolotriazole to be oxidized. More oxidant, say up to about 1.5 moles or more can be used, if desired.

The reaction is conducted in an inert reaction medium, preferably a carboxylic acid which is a liquid under the reaction temperature. Generally one uses enough liquid to obtain good contact between the reactants, while using efficient stirring. A similar method of agitation of the reaction mixture can be used, if desired. In other words, the agitation technique selected is not critical. Secondary considerations, such as those discussed above, help define the amount of inert medium employed.

The reaction is generally conducted at a temperature within the range of from about 20° C. to about 45° C.; preferably from about 25° C. to about 35° C. for from about 1 to about 3 hours.

Ambient, superatmospheric and subatmospheric pressures can be used; preferably the reaction pressure is 1 to about 100 atmospheres. Reaction times are usually between about 0.5 to about 5.0 hours. Such oxidation as discussed above can be extended to oxidation of pyrazolo-1,3,4-triazoles having acyl groups in both the 1-position and the 7-position, by using more oxidant so that both groups are oxidized.

As stated above, the pyrazolo-1,2,4-triazoles and pyrazolo-1,3,4-triazoles having an acyloxy group in the 7-position can be hydrolyzed to substituted an HO-group in that position. For example, hydrolysis of 4.0 grams of the 7-acetoxy compound produced in the previous example, in 120 ml of $CH_3OH$, was conducted using 16 milliliters of conc. HCl. The vessel containing the slurry was flushed with nitrogen, and the reaction contents were heated at reflux for 15-20 minutes under $N_2$. After that period, reaction was essentially complete.

The product was recovered as an off-white solid using a rotary evaporator, and vacuum.

The method of hydrolysis is not critical, and hydrolysis reaction conditions used in the art to prepare compounds which may have appreciable water solubility, and some degree of instability, can be employed. Generally, one uses at least enough water to conduct the hydrolysis. In other words, a stoichiometeric amount or an excess can be used. The hydrolysis may be conducted in the presence of solvent quanties of a material miscible with water, e.g. an alcohol such as ethanol. The hydrolysis is preferentially conducted in the presence of an acid catalyst, such as hydrochloric acid or similar substance. The hydrolysis can also be conducted using base catalysis; a suitable base is 0.1N sodium or potassium hydroxide. The hydrolysis may be conducted at ambient temperature or slightly elevated temperature, e.g. up to about 75° C. or higher. The process is conducted for from about 0.1 to about 10 hours. This technique can also be used to conduct the hydrolysis exemplified by Example 3 above.

A skilled practitioner aware of the detailed description herein, can make many substitutions or modifications of the embodiments described above, without departing from the scope and spirit of the appended claims.

We claim:

1. Process for the preparation of a pyrazolotriazole having the formula:

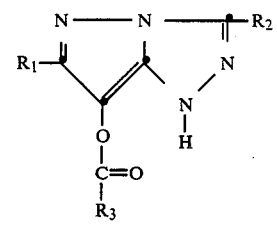

wherein $R_1$ is hydrogen or a hydrocarbyl group having up to about 20 carbon atoms, $R_2$ is a group having the formula:

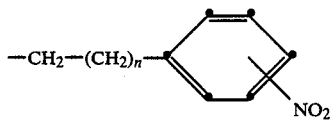

wherein n is a small whole number having a value of 0 to 6, and

R₃ is an alkyl or aryl group having up to about 20 carbon atoms;

said process comprising reacting a compound having the formula:

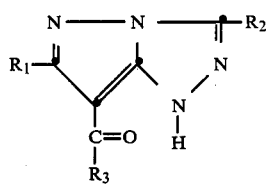

wherein

R₁, R₂, and R₃ have the same significance as above, with an oxidant selected from the class consisting of peroxymonosulfuric acid, the sodium or potassium salt thereof, the oxidant mixture $K_2S_2O_8$, $H_2SO_4$ and $K_2SO_4$, and the oxidant mixture $2KHSO_5 \cdot KHSO_4 \cdot K_2SO_4$.

2. Process of claim 1 for the preparation of 7-acetoxy-6-methyl-3-[3-(4-nitrophenyl)propyl]-1H-pyrazolo[5,1-C]-1,2,4-triazole, said process comprising oxidizing the corresponding 7-acetyl compound with the oxidant substance $2KH_5O_5 \cdot KHSO_4 \cdot K_2SO_4$.

3. The process of claim 1 wherein $R^2$ is 3-(4-nitrophenyl)-propyl.

4. The process of claim 1 wherein $R^3$ is methyl or ethyl.

5. The process of claim 1 wherein said oxidant is the oxidant mixture $2KHSO_5 \cdot KHSO_4 \cdot K_2SO_4$.

6. The process of claim 1, being conducted in a non-oxidizing carboxylic acid which is a liquid at the reaction temperature.

7. The process of claim 1, being conducted at a reaction temperature of from about 20° C. to about 45° C.

8. The process of claim 2 wherein said 7-acetoxy-6-methyl-3-[3-(4-nitrophenyl)propyl]-1H-pyrazolo[5,1-C]-1,2,4-triazole is subsequently hydrolyzed.

9. 1,7-Dimethylsulfonyl-6-methyl[-3-[3-(4-nitrophenyl)propyl]-1-H-pyrazolo[5,1-C]-1,2,4-triazole. ]

10. 1,7-Diacetyl-6-methyl[-3-[3-(4-nitrophenyl)-propyl]-1H-pyrazolo[5,1-C]-1,2,4-triazole.

11. 7-Acetyl-6-methyl-3-[3-(4-nitrophenyl)-propyl]-1H-pyrazolo[5,1-C]-1,2,4-triazole.

12. 7-Acetoxy-6-methyl-3-[3-(4-nitrophenyl)-propyl]-1H-pyrazolo[5,1-C]-1,2,4-triazole.

* * * * *